US008178511B1

(12) United States Patent
Smith

(10) Patent No.: US 8,178,511 B1
(45) Date of Patent: May 15, 2012

(54) METHOD OF ADMINISTERING HYALURONAN FORMULATION FOR THE AMELIORATION OF OSTEOPENIA

(76) Inventor: James D. Smith, Lexington, KY (US)

( * ) Notice: Subject to any disclaimer, the term of this patent is extended or adjusted under 35 U.S.C. 154(b) by 294 days.

(21) Appl. No.: 12/485,596

(22) Filed: Jun. 16, 2009

Related U.S. Application Data

(60) Provisional application No. 61/077,740, filed on Jul. 2, 2008.

(51) Int. Cl.
*A61H 31/728* (2006.01)
*C07H 5/06* (2006.01)

(52) U.S. Cl. .......................... 514/54; 536/53; 536/55.1

(58) Field of Classification Search .................... 514/54; 536/55.1, 123.1
See application file for complete search history.

(56) References Cited

U.S. PATENT DOCUMENTS

| | | | |
|---|---|---|---|
| 4,623,539 A | 11/1986 | Tunc | |
| 4,647,453 A | 3/1987 | Meisner | |
| 4,808,576 A * | 2/1989 | Schultz et al. ................... | 514/54 |
| 5,095,037 A * | 3/1992 | Iwamitsu et al. ............. | 514/561 |
| 5,843,919 A | 12/1998 | Burger | |
| 5,985,850 A | 11/1999 | Falk et al. | |
| 6,013,641 A | 1/2000 | Lussow et al. | |
| 6,162,787 A | 12/2000 | Sorgente et al. | |
| 6,255,295 B1 | 7/2001 | Henderson et al. | |
| 6,333,304 B1 | 12/2001 | Bath et al. | |
| 6,346,519 B1 | 2/2002 | Petrus | |
| 6,387,382 B1 | 5/2002 | Saleh et al. | |
| 6,391,861 B1 | 5/2002 | Cantor | |
| 6,391,864 B1 | 5/2002 | Stone | |
| 6,432,929 B1 | 8/2002 | Stone | |
| 6,451,771 B1 | 9/2002 | Henderson et al. | |
| 6,476,005 B1 | 11/2002 | Petito et al. | |
| 6,537,978 B1 | 3/2003 | Turley | |
| 6,607,745 B2 | 8/2003 | Leneau | |
| 6,608,041 B2 | 8/2003 | Hammerly | |
| 6,620,927 B2 | 9/2003 | Bulpitt et al. | |
| 6,645,945 B1 * | 11/2003 | Radomsky et al. ............. | 514/54 |
| 6,706,267 B1 | 3/2004 | Adalsteinsson et al. | |
| 6,924,273 B2 | 8/2005 | Pierce | |
| 6,979,679 B2 | 12/2005 | Marcum | |
| 7,811,612 B2 | 10/2010 | Kim et al. | |

OTHER PUBLICATIONS

Stancikova et al. Int. J. Tissue React, 2004, 26(1/2), p. 9-16.*
United States Patent and Trademark Office; Office Action; mailed Oct. 26, 2010; in U.S. Appl. No. 12/572,641.
Response to Office Action in U.S. Appl. No. 12/572,641, electronically filed Jan. 24, 2011.
James D. Smith, "Method of Administering Hyaluronan Formulation for the Amelioration of Osteoarthritis", U.S. Appl. No. 12/165,278, filed Jun. 30, 2008, (Pending).
James D. Smith, "Method of Administering Hyaluronan Formulation for the Amelioration of Osteoarthritis", U.S. Appl. No. 12/572,641, filed Oct. 2, 2009, (Pending).
James D. Smith, "Method of Administering Hyaluronan Formulation for the Amelioration of Osteophytes", U.S. Appl. No. 12/485,265, filed Jun. 16, 2008, (Pending).
James D. Smith, "Hyaluronan Formuation", U.S. Appl. No. 11/595,657, filed Nov. 11, 2006, (Abandoned).
Office Action mailed Sep. 14, 2008 in U.S. Appl. No. 11/595,657.
Response to Office Action mailed Sep. 14, 2008 and electronically submitted on Mar. 13, 2009.
Office Action mailed Jul. 23, 2009 in U.S. Appl. No. 11/595,657.
Mary K. Cowman. "$^1$H NMR of Glycosaminoglycans and Hyaluronic Acid Oligosaccharirdes in Aqueous Solution: The Amide Proton Environment", Archives of Biochemistry and Biophysics. vol. 230, No. 1, pp. 203-212, Apr. 1984.
Mary K. Cowman, "$^1$H NMR of Glycosaminoglycans and Hyaluronic Acid Oligosaccharirdes in Aqueous Solution: The Amide Proton Environment", Archives of Biochemistry and Biophysics. vol. 230, No. 1, pp. 203-212, Apr. 1984, (Abstract only).
M.F. McCarty, et al., "Sulfated Glycosaminoglycans and Glucosamine May Synergize in Promoting Synovial Hyaluronic Acid Synthesis", Medical Hypothesis (2000) 54(5), 798-802, Mar. 17, 1999.
M. Anthony Pogrel, et al., Hyaluronan (hyaluronic acid) in Human Saliva, Archives of Oral Biology, vol. 41, No. 7, pp. 667-671, (1996).
A Rossler, et al., "Plasma Hyaluronan Concentration: No Circadian Rhythm but Large Effect of Food Intake in Humans", Eur J Appl Physiol, vol. 78, No. 6, pp. 573-577, (1998).
Hideki Sato, et al., Antioxidant Activity of Synovial Fluid, Hyaluronic Acid, and Two Subcomponents of Hyaluronic Acid, Arthritis and Rheumatism, vol. 31, No. 1 (Jan. 1998).
Chris Tuckwell, "Velvet Antler, a Summary of the Literature on Health Benefits", Australian Government—Rural Industries Research and Development Corporation, Nov. 2003.
M.Anthony Pogrel, et al., "Hyaluronan (hyaluronic acid) and Its Regulation in Human Saliva by Hyaluronidase and its Inhibitors", Journal of Oral Science, vol. 45. No. 2, 2003, pp. 85-91, Publication Date: May 19, 2003.

* cited by examiner

*Primary Examiner* — Shaojia Anna Jiang
*Assistant Examiner* — Jonathan S Lau
(74) *Attorney, Agent, or Firm* — Curatolo Sidoti Co., LPA; Salvatore A. Sidoti

(57) ABSTRACT

Disclosed is a method for the amelioration of resorptive bone loss in osteopenia including administering to a subject a therapeutically effective amount of an exogenous hyaluronan formulation.

17 Claims, 6 Drawing Sheets

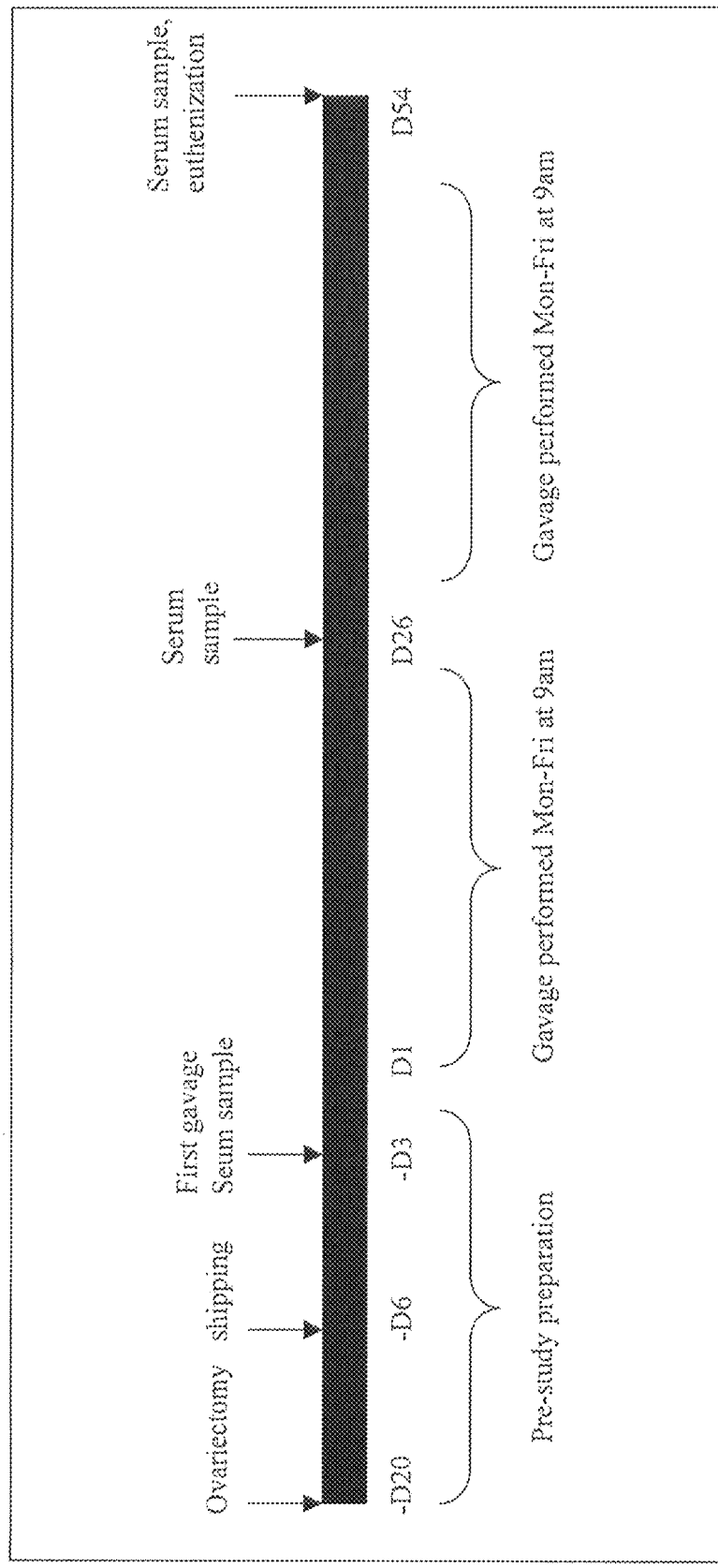
Figure 1. Schematic of treatment schedule

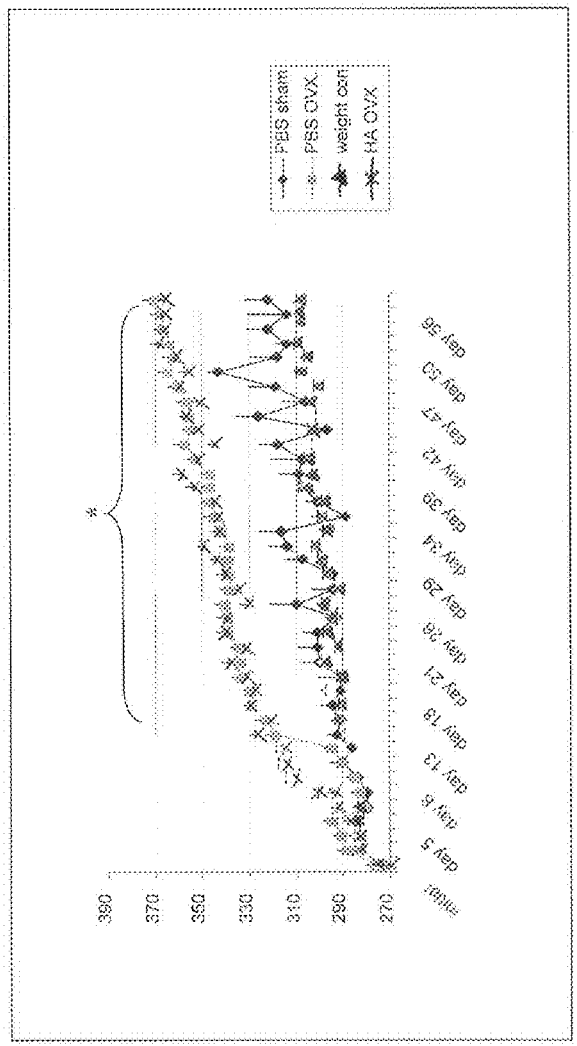
Figure 2. Weight gain of rats following ovariectomy and treatment with hyaluronan or PBS

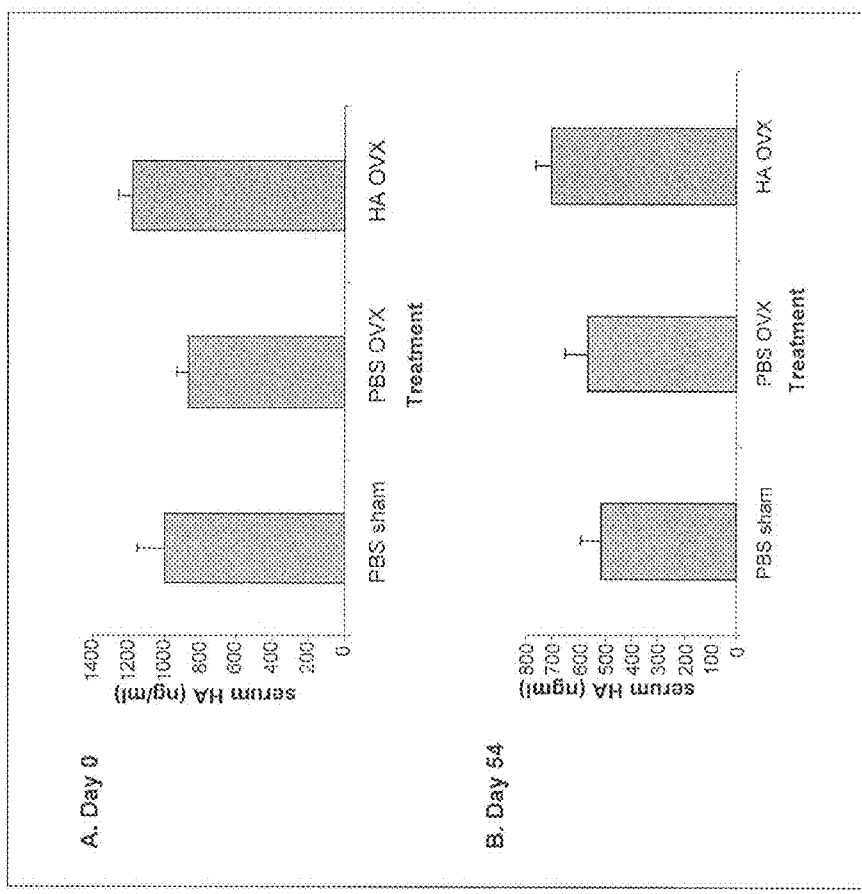

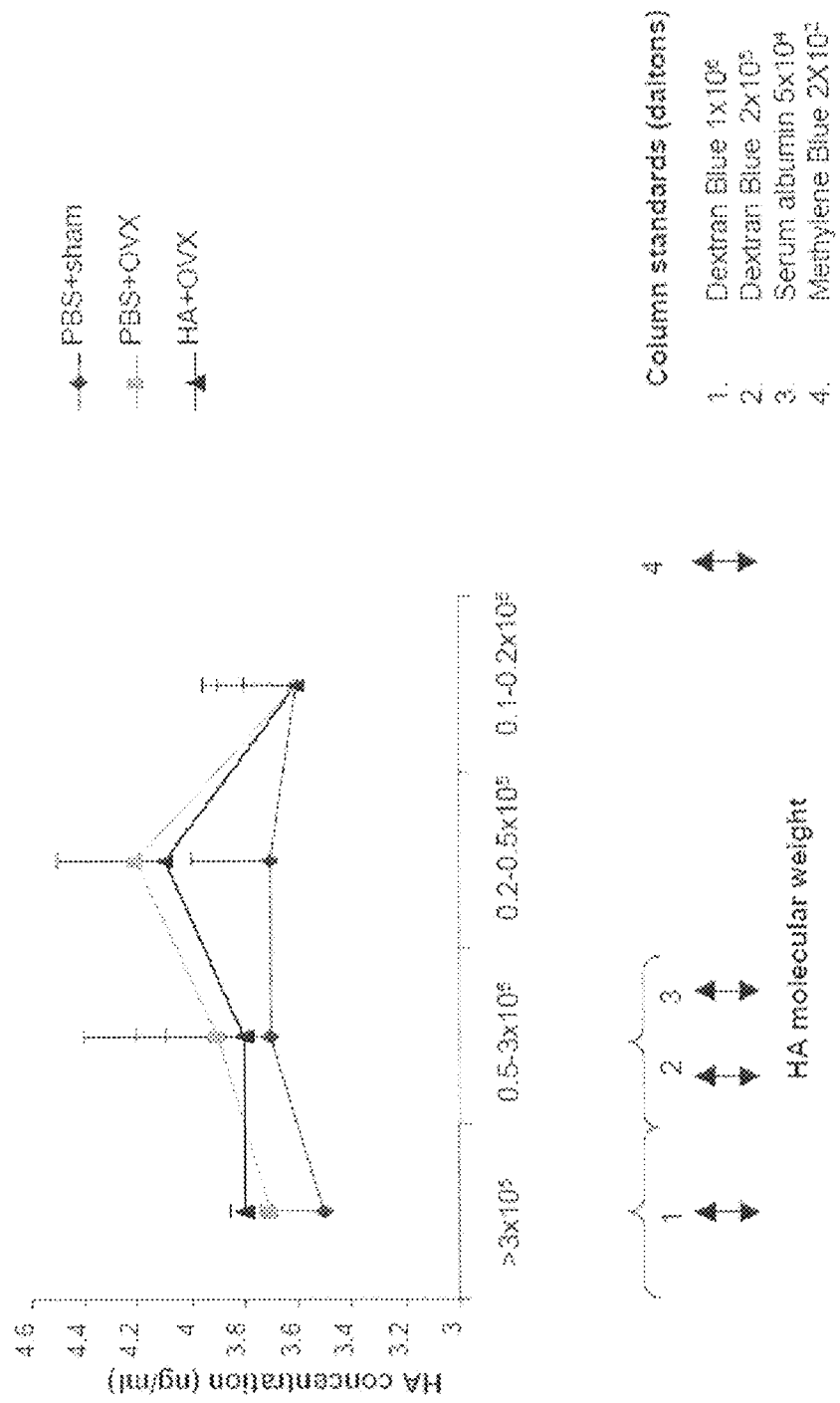

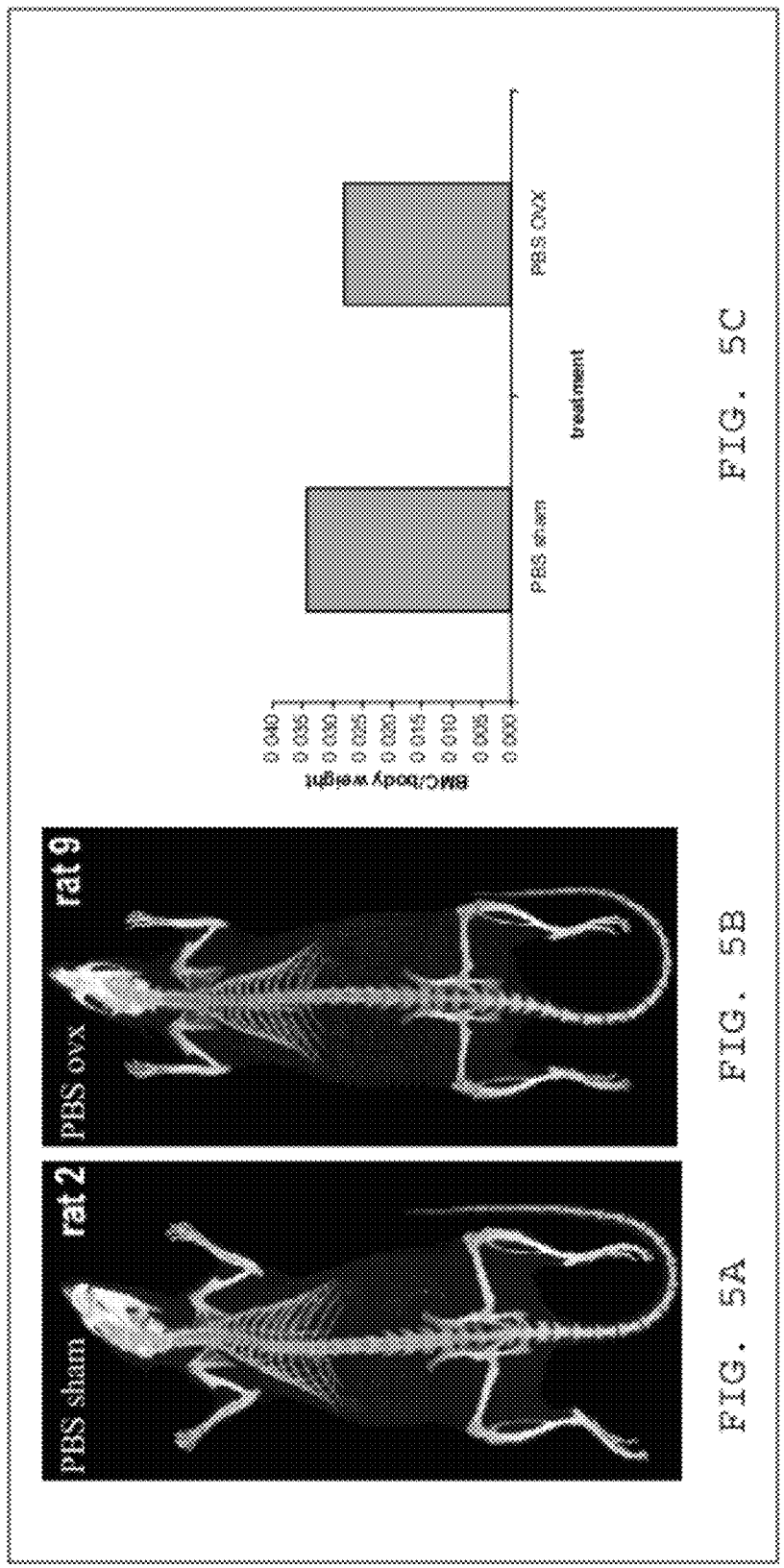

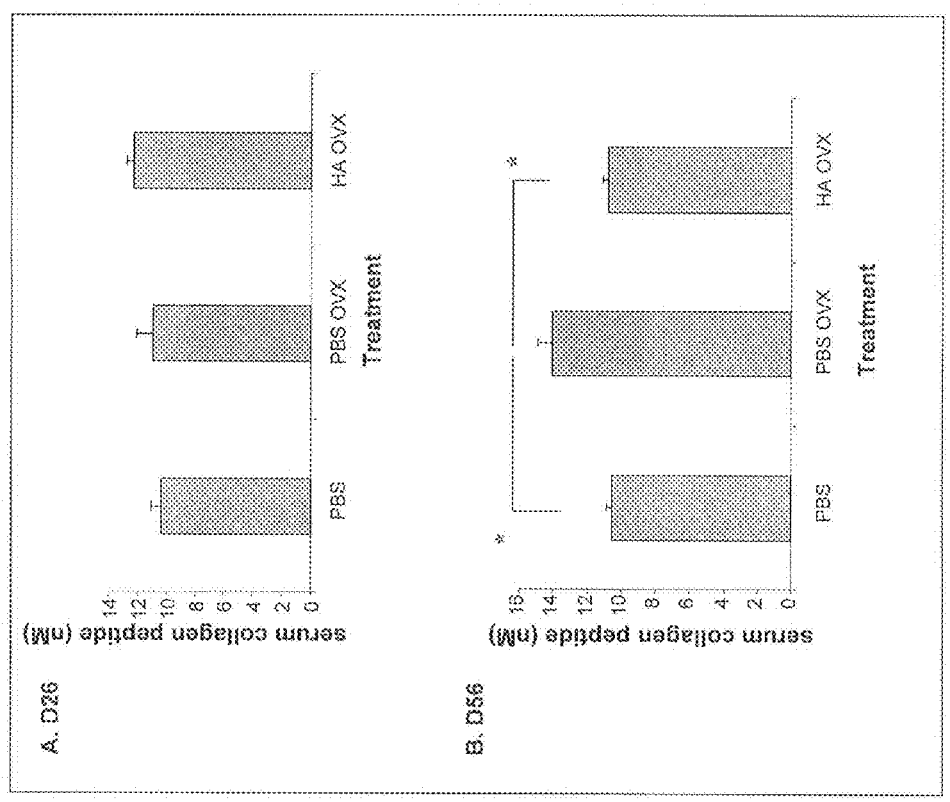
Figure 6. Serum collagen tripeptide levels in sham operated and PBS or HA-treated ovariectomized rats

METHOD OF ADMINISTERING HYALURONAN FORMULATION FOR THE AMELIORATION OF OSTEOPENIA

CROSS REFERENCE TO RELATED APPLICATIONS

This application claims the benefit of the filing date under 35 U.S.C. §119(e) of U.S. Provisional Application For Patent Ser. No. 61/077,740 filed on Jul. 2, 2008, which is hereby incorporated by reference in its entirety.

TECHNICAL FIELD

The present disclosure relates to a method of administering a composition comprising a therapeutically effective amount of an exogenous hyaluronan to a vertebrate subject for preventing, slowing, attenuating, mitigating, and/or ameliorating the resorptive loss of bone mineral density in osteopenia of the subject.

BACKGROUND

Currently, an estimated 33.6 million Americans, 80% of which are women, have osteopenia, a precursor of osteoporosis typified by resorptive bone loss. Although the risk of bone fractures is significantly greater in patients with osteoporosis compared to osteopenia, the larger numbers of Americans with osteopenia make this group clinically more significant for risk for fracture. Risk factors for osteopenia include menopause, nutrition and extreme exercise. Current treatments include dietary supplements such as calcium and vitamin D, antiresorptive drugs, estrogen, selective estrogen receptor modulators, bisphonate drugs, calcitonin and anabolic drugs. However, the majority of these treatments have significant side effects or are not suitable for long-term administration.

Bone density is determined by both osteoclastic and osteoblastic activity. Although domination of osteoclastic over osteoblast proliferation/differentiation will result in net bone loss, some osteoclast activity is required for bone replacement and maintenance of normal density. Since endogenous hyaluronan has effects on both osteoclast and osteoblast function and since this is dependent in part upon its molecular weight, it would be difficult to predict the effects of exogenously administered hyaluronan on bone density, particularly since serum and tissue hyaluronidases could theoretically cleave administered hyaluronan to produce an abundance of fragments with osteoclast-activating properties. However, the precise mechanisms by which endogenous hyaluronan effects bone physiology are currently incompletely understood.

There is no teaching in the art of a method for preventing, slowing, attenuating, mitigating, and/or ameliorating the resorptive loss of bone in a vertebrate subject, the method comprising the step of administering a composition comprising a therapeutically effective amount of an exogenous hyaluronan to the subject. The instant invention provides such a method.

SUMMARY

Disclosed is a method for preventing, slowing, attenuating, mitigating, and/or ameliorating bone resorptive loss of mineral density in a vertebrate subject, the method comprising the step of administering a composition comprising a therapeutically effective amount of an exogenous hyaluronan formulation to a vertebrate subject.

BRIEF DESCRIPTION OF THE DRAWINGS

FIG. 1 is a schematic representation of a treatment schedule for a bone loss study.

FIG. 2 is a graph showing the weight gain for study rats following ovariectomy.

FIG. 3 are graphs showing serum hyaluronan levels in sham operated and ovariectomized study rats.

FIG. 4 is a graph showing the molecular weight profiles of serum hyaluronan samples of study rats.

FIG. 5A is a CT scan of a skeleton of a sham operated study rat.

FIG. 5B is a CT scan of a skeleton of an ovariectomized study rat.

FIG. 5C is a graph showing the bone mineral density of sham operated and ovariectomized study rats.

FIG. 6 are graphs of serum collagen tripeptide levels in sham operated study rats, and PBS-treated and hyaluronan-treated ovariectomized study rats.

DETAILED DESCRIPTION

Disclosed is a method of administering a modified hyaluronan biopolymer to a vertebrate subject for the purposes of preventing, slowing, attenuating, mitigating, and/or ameliorating the resorptive loss of bone mineral density in osteopenia. The method comprises administering a composition comprising a therapeutically effective amount of exogenous hyaluronan biopolymer to the subject.

The method of administering a therapeutically effective amount of the hyaluronan biopolymer to a subject may be accomplished by any means known in the art, such as, without limitation, oral or parenteral administration. According to certain illustrative embodiments, parenteral administration of the therapeutically effective amount of the hyaluronan may comprise subcutaneous administration, intramuscular administration, and intravenous administration.

A therapeutically effective amount of hyaluronan biopolymer per kg body weight of the test subject can be determined by one having ordinary skill in the art without having to resort to undue experimentation. According to certain illustrative embodiments, and without limitation, therapeutically effective amounts may comprise from about 0.2 to about 5 mg per kg body weight of the subject per day, from about 0.4 to about 4 mg per kg body weight of the subject per day, from about 0.6 to about 3 mg per kg body weight of the subject per day, from about 0.8 to about 2 mg per kg body weight of the subject per day, and about 1 mg per kg body weight of the subject per day. The daily therapeutically effective amount of the hyaluronan biopolymer may be administered to the subject as a single dose comprising the entire therapeutically effective amount. Alternatively, the therapeutically effective amount of the hyaluronan biopolymer may be achieved by administering multiple lower amounts that cumulatively achieve the daily therapeutically effective amount.

The term "hyaluronan" as used herein refers to hyaluronic acid or any physiological salt form of hyaluronic acid. The hyaluronan biopolymer may be polydisperse and therefore comprises a mixture of hyaluronan polymers having different molecular masses. In certain embodiments, the hyaluronan biopolymer is polydisperse and therefore comprises a mixture of hyaluronan polymers having different molecular masses. Without limitation, the hyaluronan biopolymer that is administered to the vertebrate subject may comprise weight average molecular weights in a range from about 50,000 to about 8,000,000 Daltons. By way of illustration, suitable hyaluronan may comprise molecular weights from about 500,000 to about 2,500,000 Daltons, from about 750,000 to about 2,250,000 Daltons, from about 1,000,000 to about 2,000,000 Daltons, from about 1,250,000 to about 1,750,000 Daltons, or from about 1,375,000 to about 1,625,000 Daltons. According to certain embodiments, the biopolymer comprises an average molecular weight of about 1,500,000 Daltons.

Without limitation, the physiological salt form may comprises an alkali metal salt. For example, according to an illustrative embodiment, the physiological salt may comprise sodium hyaluronate.

According to illustrative embodiments, the biopolymer composition comprises a product of microbial fermentation. By producing the polymer by extra-cellular microbial fermentation, it is considered to be a vegan product. Accordingly, the hyaluronan may contain no animal derived materials, which minimizes the risk of transmission of animal spongiform encephalopathy. Producing the hyaluronan polymer by microbial fermentation also results in more consistent molecular profile, molecular weight and narrow polydispersity that is optimized for oral bioavailability.

The hyaluronan composition comprises a pharmaceutically acceptable carrier that is safe for human or veterinary consumption. Without limitation, and by way of example only, a suitable carrier for the hyaluronan composition is water.

The hyaluronan composition further comprises at least one pharmaceutically acceptable excipient. Without limitation, and by way of example only, a suitable excipient for the hyaluronan composition comprises sodium chloride.

The hyaluronan composition may also include a pH altering agent. Without limitation, and by way of example only, a suitable pH altering agent for the hyaluronan composition comprises citric acid. According to certain embodiments, and without limitation, citric acid is included in the hyaluronan composition in an amount effective to provide a pH of the hyaluronan composition that is between about 2.5 and about 4.5.

According to certain illustrative embodiments, the composition comprises a therapeutically effective amount of hyaluronan and an antimicrobial preservative. Any known antimicrobial preservative that is generally regarded as safe for human or veterinary consumption may be included in the hyaluronan composition. Without limitation, suitable antimicrobial preservatives include potassium sorbate, sodium benzoate and mixtures thereof.

The biopolymer composition and method of administration may be useful for preventing bone loss in a wide variety of vertebrate species. For example, and by way of example only, the hyaluronan composition may be administered to any of human, equine, canine or feline species.

The hyaluronan may be formulated into a wide variety of orally ingestible compositions. The hyaluronan may be formulated with an acceptable carrier to provide an orally ingestible liquid or a solid or semi-solid food product. Liquid forms include solutions, suspensions, emulsions, syrups and the like. According to certain illustrative embodiments, the hyaluronan composition may be formulated with an orally ingestible liquid carrier to provide an orally ingestible hyaluronan composition. For example, the hyaluronan may be formulated with an orally ingestible liquid carrier to provide a beverage, dietary supplement formulation, or nutritional supplement. The beverages, dietary supplements and nutritional supplements may be provided ready for oral ingestion or may be provided in a concentrate that requires dilution with acceptable liquids prior to oral ingestion. According to alternative embodiments, the hyaluronan may be formulated into other orally ingestible product forms, such as powders, pills, lozenges, tablets, caplets, capsules, gel capsules and the like. Flavoring agents may also be added to the hyaluronan compositions to provide a more palatable orally ingestible composition.

The orally administrable hyaluronan composition may further include nutritionally effective amounts of an additional supplement. According to certain embodiments, the hyaluronan composition further comprises nutritionally effective amounts of at least one vitamin, or at least one mineral or a combination of at least one vitamin and at least one mineral. According to certain embodiments, the hyaluronan composition comprises a therapeutically effective amount of hyaluronan and a nutritionally effective amount of at least one vitamin. According to certain embodiments, the hyaluronan composition comprises a therapeutically effective amount of hyaluronan and a nutritionally effective amount of more than one different vitamin. According to certain embodiments, the hyaluronan composition comprises a therapeutically effective amount of hyaluronan and a nutritionally effective amount of at least one mineral. According to certain embodiments, the hyaluronan composition comprises a therapeutically effective amount of hyaluronan and a nutritionally effective amount of more than one different mineral. According to certain embodiments, the hyaluronan composition comprises a therapeutically effective amount of hyaluronan and a nutritionally effective amount of at least one vitamin and at least one mineral. According to certain embodiments, the hyaluronan composition comprises a therapeutically effective amount of hyaluronan and a nutritionally effective amount of more than one different vitamin and at least one mineral. According to certain embodiments, the hyaluronan composition comprises a therapeutically effective amount of hyaluronan and a nutritionally effective amount of at least one vitamin and more than one different mineral. According to certain embodiments, the hyaluronan composition comprises a therapeutically effective amount of hyaluronan and a nutritionally effective amount of more than one different vitamin and more than one different mineral.

The hyaluronan composition may also include a drug component alone or in addition to the nutritional supplement.

EXAMPLES

The following examples are provided to further illustrate the hyaluronan composition and method of administering the exogenous hyaluronan to vertebrate subjects. It should be noted that the examples are provided for illustration and should not be construed to limit the scope of the composition or method of administering the composition in any manner.

Evaluation of MHB3™ on the Development of Osteopenia

Osteopenia is a common bone loss condition preceding frank osteoporosis, and is often associated with estrogen depletion. N-terminal collagen peptides in serum are increased with osteopenia. Elisa analysis of elevated collagen peptide levels using monoclonal antibodies to detect the peptides is used clinically to measure response to bone building medications and is an accepted measure of osteopenia. The effects of oral MHB3 M™ (modified hyaluronan) supplementation on bone loss were investigated in an established model of osteopenia using ovariectomized (OVX) female rats.

Female Sprague Dawley rats (N=25) were purchased from Charles River Laboratories. Three (3) rats served as untreated weight controls. Seventeen (17) rats received bilateral OVX and were randomized into 2 groups. The OVX placebo (PBS) group (N=5) was gavaged with physiological saline 5 days/week, the OVX treatment group (N=12) was gavaged with 1.0 mg MHB3™/kg 5 days/week. Five (5) rats received sham surgeries and were gavaged 1×PBS 5 days/week. Blood (0.3 ml) was drawn from rats' tail veins 3 days prior to commencing gavage and at D26 and D54. Blood was centrifuged and the resulting sera was immediately stored at −20° C. Peptide levels were measured using a competitive-inhibition enzyme-linked immunosorbent assay for qualifying serum collagen N-terminal peptides (Osteomark NTx kit). Assays were performed according to the manufacturer's instructions.

By D14, PBS OVX animals had gained significantly more weight than PBS Sham animals. MHB3™ treated animals exhibited the same weight gain as PBS control animals. Serum collagen levels in PBS sham, PBS OVX, and MHB3™ OVX animals were analyzed at D26 and D54. Serum collagen peptide levels at D26 were similar in all three groups suggesting that significant bone loss had not yet occurred. However, by D54 serum collagen peptide levels had significantly increased in PBS OVX animals compared to PBS sham. Micro-CT scans confirmed that significant bone loss had occurred at this time. MHB3™ OVX animals also exhibited serum peptide levels that were significantly less than PBS-OVX animals suggesting a protective effect of MHB3™ in osteopenia. Accordingly, a hyaluronan formulation administered 5 days/week by oral gavage significantly reduces the development of osteopenia associated with estrogen depletion, as detected by levels of N-terminal collagen peptides in serum.

Likewise, through parenteral administration of a buffered hyaluronan solution, such as through subcutaneous or intramuscular administration, similar effects are observed. It will be apparent to those skilled in the art to which the present invention pertains how to make and how to use such a buffered hyaluronan solution for parenteral administration.

While the method for administering hyaluronan to vertebrate subject has been described above in connection with certain illustrative embodiments, it is to be understood that other embodiments may be used or modifications and additions may be made to the described embodiments for performing the same function without deviating therefrom. Furthermore, all embodiments disclosed are not necessarily in the alternative, as various embodiments may be combined to provide the desired characteristics. Variations can be made by one having ordinary skill in the art without departing from the spirit and scope of the disclosed method. Therefore, the method should not be limited to any single embodiment, but rather construed in breadth and scope in accordance with the recitation of the attached claims. Equivalents will be readily apparent to those skilled in the art.

I claim:

1. A method for slowing, attenuating, mitigating, and/or ameliorating the loss of bone mineral density in a vertebrate subject, the method comprising orally administering to the subject a composition comprising a therapeutically effective amount of polydisperse hyaluronan comprising a blend of hyaluronan polymers having different molecular masses and a carrier, wherein the pH of the composition is between about 2.5 and about 4.5.

2. The method of claim 1, wherein the composition comprises from about 0.2 to about 5 mg hyaluronan per kg body weight of the subject per day.

3. The method of claim 2, wherein the composition comprises from about 0.4 to about 4 mg hyaluronan per kg body weight of the subject per day.

4. The method of claim 3, wherein the composition comprises from about 0.6 to about 3 mg hyaluronan per kg body weight of the subject per day.

5. The method of claim 4, wherein the composition comprises from about 0.8 to about 2 mg hyaluronan per kg body weight of the subject per day.

6. The method of claim 5, wherein the composition comprises about 1 mg hyaluronan per kg body weight of the subject per day.

7. The method of claim 1, wherein the carrier comprises water.

8. The method of claim 1, wherein the excipient comprises sodium chloride.

9. The method of claim 1, wherein the composition comprises citric acid.

10. The method of claim 1, wherein the hyaluronan comprises molecular weights from about 500,000 to about 2,500,000 Daltons.

11. The method of claim 10, wherein the hyaluronan comprises molecular weights from about 750,000 to about 2,250,000 Daltons.

12. The method of claim 11, wherein the hyaluronan comprises molecular weights from about 1,000,000 to about 2,000,000 Daltons.

13. The method of claim 12, wherein the hyaluronan comprises molecular weights from about 1,250,000 to about 1,750,000 Daltons.

14. The method of claim 13, wherein the hyaluronan comprises molecular weights from about 1,375,000 to about 1,625,000 Daltons.

15. The method of claim 14, wherein the hyaluronan is of median molecular weight about 1,500,000 Daltons.

16. The method of claim 1, wherein the hyaluronan is a product of microbial fermentation.

17. The method of claim 1, wherein the composition comprises an antimicrobial preservative.

* * * * *